(12) United States Patent
McKinney et al.

(10) Patent No.: US 12,380,992 B2
(45) Date of Patent: Aug. 5, 2025

(54) SYSTEM AND METHOD FOR INTERPRETATION OF MULTIPLE MEDICAL IMAGES USING DEEP LEARNING

(71) Applicant: Google LLC, Mountain View, CA (US)

(72) Inventors: Scott McKinney, San Francisco, CA (US); Marcin Sieniek, Mountain View, CA (US); Varun Godbole, Mountain View, CA (US); Shravya Shetty, San Francisco, CA (US); Natasha Antropova, London (GB); Jonathan Godwin, London (GB); Christopher Kelly, London (GB); Jeffrey De Fauw, London (GB)

(73) Assignee: Google LLC, Mountain View, CA (US)

( * ) Notice: Subject to any disclaimer, the term of this patent is extended or adjusted under 35 U.S.C. 154(b) by 516 days.

(21) Appl. No.: 17/597,876

(22) PCT Filed: Jun. 16, 2020

(86) PCT No.: PCT/US2020/037880
§ 371 (c)(1),
(2) Date: Jan. 27, 2022

(87) PCT Pub. No.: WO2021/021329
PCT Pub. Date: Feb. 4, 2021

(65) Prior Publication Data
US 2022/0254023 A1    Aug. 11, 2022

Related U.S. Application Data

(60) Provisional application No. 62/880,793, filed on Jul. 31, 2019, provisional application No. 62/891,598, filed on Aug. 26, 2019.

(51) Int. Cl.
*G16H 30/40*    (2018.01)
*G06T 7/00*    (2017.01)
(Continued)

(52) U.S. Cl.
CPC .......... *G16H 30/40* (2018.01); *G06T 7/0014* (2013.01); *G06V 10/22* (2022.01); *G06V 10/82* (2022.01);
(Continued)

(58) Field of Classification Search
CPC ...... G16H 30/40; G16H 50/20; G06T 7/0014; G06T 2207/10081; G06T 2207/20084;
(Continued)

(56) References Cited

U.S. PATENT DOCUMENTS

2007/0167697 A1\* 7/2007 Avila ................... G01T 1/1611
600/407
2018/0263568 A1\* 9/2018 Yi .......................... A61B 5/202
(Continued)

OTHER PUBLICATIONS

Perek et al, "Siamese Network for Dual-View Mammography Mass Matching" (published at Springer Nature Switzerland AG 2018, pp. 55-63, Jul. 2018).\*
(Continued)

*Primary Examiner* — Casey L Kretzer
(74) *Attorney, Agent, or Firm* — McDonnell Boehnen Hulbert & Berghoff LLC

(57) ABSTRACT

A method is disclosed of processing a set of images. Each image in the set has an associated counterpart image. One or more regions of interest (ROIs) are identified in one or more of the images in the set of images. For ROI identified, a reference region is identified in the associated counterpart image. ROIs and associated reference regions are cropped out, thereby forming cropped pairs of images 1 ... $n_1$, that are fed to a deep learning model trained to make a prediction of probability of a state of the ROI, e.g., disease state, which generates a prediction $P_i$-, (i=1 ... n) for each cropped pair. The model generates an overall prediction P from each of the predictions $P_i$. A visualization of the set of medical images and the associated counterpart images including the cropped pair of images is generated.

13 Claims, 3 Drawing Sheets

(51) Int. Cl.
*G06V 10/22* (2022.01)
*G06V 10/82* (2022.01)
*G16H 50/20* (2018.01)

(52) U.S. Cl.
CPC ... *G16H 50/20* (2018.01); *G06T 2207/10081* (2013.01); *G06T 2207/20084* (2013.01); *G06T 2207/20132* (2013.01); *G06T 2207/30061* (2013.01); *G06T 2207/30068* (2013.01)

(58) Field of Classification Search
CPC . G06T 2207/20132; G06T 2207/30061; G06T 2207/30068; G06V 10/22; G06V 10/82
See application file for complete search history.

(56) References Cited

U.S. PATENT DOCUMENTS

| | | | |
|---|---|---|---|
| 2020/0185084 A1* | 6/2020 | Syeda-Mahmood | G06V 10/7515 |
| 2020/0202524 A1* | 6/2020 | Karki | G06T 7/0012 |

OTHER PUBLICATIONS

Han, et al., "The Classification of Renal Cancer in 3-Phase CT Images Using a Deep Learning Method", Journal of Digital Imaging, 32:638-643 (2019).

Kumar et al., "Co-Learning Feature Fusion Maps from PET-CT Images of Lung Cancer", IEEE TMI, http://dx.doi.org/10.1109/TMI.2019.2923601 (2019).

Perek et al., "Siamese Network for Dual-View Mammography Mass Matching", Abstract Only, Rambo (2018).

Rodriguez-Ruiz et al., "Detection of Breast Cancer with Mammography: Effect of an Artificial Intelligence Support System", Radiology, pp. 1-10 (2019).

Vaswani et al., "Attention is All You Need", 31st Conference on Neural Information Processing Systems (2017).

International Search Report for corresponding PCT application No. PCT/US2020/037880, dated Sep. 8, 2020.

Vaswani et al., "Attention Is All You Need," 31st Conference on Neural Information Processing Systems (NIPS 2017), Long Beach, CA, USA, arXiv:1706.03762v5, Dec. 6, 2017, 15 pages.

European Patent Office, Office Action mailed Oct. 2, 2024, issued in connection with European Patent Application No. 20735801.1, 11 pages.

Hagos et al., "Improving Breast Cancer Detection using Symmetry Information with Deep Learning", arXiv:1808.08273v1, Aug. 17, 2018, 8 pages.

Hupse et al., "Use of Normal Tissue Context in Computer-Aided Detection of Masses in Mammograms," IEEE Transactions on Medical Imaging, 2009, pp. 2033-2041, vol. 28, No. 12.

Kooi et al., "Classifying symmetrical differences and temporal change for the detection of malignant masses in mammography using deep neural networks," Journal of Medical Imaging, Oct.-Dec. 2017, 10 pages, vol. 4, No. 4.

Wu et al., "Bilateral analysis based false positive reduction for computer-aided mass detection", Medical Physics, Aug. 2007, pp. 3334-3344, vol. 34, No. 8.

\* cited by examiner

SYSTEM AND METHOD FOR INTERPRETATION OF MULTIPLE MEDICAL IMAGES USING DEEP LEARNING

PRIORITY

This present application claims priority as a U.S. national stage entry of PCT application serial no. PCT/US2020/037880 filed Jun. 16, 2020, which claims priority to U.S. provisional application Ser. No. 62/880,793 filed Jul. 31, 2019, and to U.S. Provisional application Ser. No. 62/891,598 filed Aug. 26, 2019. The full disclosure of each aforementioned prior filed application is incorporated herein by reference.

BACKGROUND

This disclosure relates to a method and system for interpretation of multiple medical images using deep learning. The methods can be implemented in an artificial intelligence-based system to help improve cancer detection and screening.

The method is suitable for use with a variety of imaging datasets, including, for example, mammograms obtained from conventional mammography equipment, computed tomography (CT) datasets for lung cancer detection from CTs, and multimodal magnetic resonance imaging (MRI) for prostate cancer detection. The method and system may be implemented using deep learning methods.

Longitudinal and multimodal imaging techniques help improve cancer screening diagnosis. "Longitudinal imaging" refers to prior patient images being available for comparison to a current or most recent image in detecting and diagnosing cancer. "Multimodal MRI" is used to refer to multiple pulse-sequences taken during a single Magnetic Resonance Imaging (MRI) study. The term "multimodal imaging" is also used to refer to obtaining different types of images of a subject, such as MRI, CT scans, and positron emission tomography (PET), and such images of a subject may or may not be obtained at the same time.

SUMMARY

In a first aspect, a method of processing a set of medical images is described. Each image in the set has an associated counterpart image, for example, a contralateral image, an image of the same area obtained by a different imaging modality, or a prior image of the same area. In a mammography example, the set of images could be a set of three or four images obtained from the left breast in three or four different orientations (conventional) and the associated counterpart images are contralateral images of the right breast obtained in the same orientations. The method includes steps of:

a) identifying one or more regions of interest (e.g., potentially cancerous lesions) in one or more of the images in the set of images;

b) for each region of interest identified in step a), identifying a (respective) reference region in the associated counterpart image; note that the image containing the region of interest may be registered with the corresponding counterpart image, and at least one re-orientating step may be performed to bring the counterpart image into alignment with the image containing the region of interest; following this registration and any reorienting, the reference region will typically correspond spatially to the region of interest (e.g. the region or interest and reference may each appear to show the same anatomical structure, viewed from the same orientation);

c) cropping out the regions of interest and the reference regions identified in step b) from their respective images, thereby forming cropped pairs of images 1 . . . n. That is, if there are for example four images in the set, and four corresponding counterpart images, there could for example be 3 regions of interest identified in each of the four images in the set; each region of interest in each image has its associated reference region in the corresponding contralateral image, therefore n=12 (4×3) in this example.

d) feeding the cropped pairs of images from step c) to a deep learning model trained to make a prediction of probability of disease state and generating a prediction Pi, (i=1 . . . n) for each cropped pair;

e) generating an overall disease prediction P from each of the predictions Pi; and f) generating a visualization of the set of medical images and the associated counterpart images including portions of the images corresponding to the cropped pair of images.

In one embodiment, the associated counterpart image is a contralateral image. In one possible embodiment, the set of medical images is in the form of a set of mammogram images of a single subject, and wherein the associated counterpart images are contralateral images to the set of mammogram images.

Alternatively, the counterpart images are longitudinal images, or images obtained by an imaging modality which is different from the modality used to generate the set of images. For example, the set of images may generated using a first imaging modality selected from the set consisting of X-ray, ultrasound, MRI, CT, PET scanning, and the counterpart images may be generated using a second, different imaging modality selected from the same set of imaging modalities.

The portions of the images corresponding to at least one cropped pair of images may be presented in the visualization in a manner dependent upon P and/or upon the corresponding Pi.

In one embodiment, the visualization generated in step f) further includes information indicating the manner in which a cropped pair of images contributed to the overall disease prediction. For example, the information may be whether the value of Pi is above or below a specified (e.g. pre-determined) threshold, and/or within a specified range, or whether, due to the presence in the equation for P of the term relating to the region of interest (i.e. the term including Pi), the value of P was changed by an amount which was above or below a specified threshold, and/or within a specified range. For example, the information could be presented in the form of color coding of bounding boxes superimposed on display of the images and counterparts images, with the bounding boxes showing the ROI and reference region and color coding identifying whether the ROI+reference region pair contributed positively, negatively or neutrally to the prediction. The visualization could also include plain text which includes this information.

In one embodiment, the deep learning model takes the form of a deep convolutional neural network which includes a feature extractor, a self-attention mechanism (e.g. arranged to receive an output of the feature extractor) and a concatenation of information as to the global location of the region of interest to thereby inject global context information into the generation of the prediction Pi. By "concatenation of information" is meant that a layer of the neural network (e.g. an output layer which generates the values Pi) receives data generated by the self-attention mechanism and also the information indicating the global location of the same region of interest (e.g. information indicating the position of the region of interest within the image containing the region of interest, such as information indicating the position of the part of the anatomy shown in the region of interest within a larger anatomical structure shown by the image containing the region of interest).

The visualization generated in the method is useful to a human user (e.g. a pathologist or radiologist) in making a diagnosis, e.g. of cancer. For example, the human user can see how the regions of interest which had a significant influence on the value of P are distributed over the anatomical structure imaged by the set of images. The human user may use this information (e.g. in combination with other information the human user may have access too, such as blood test results) to form a judgement about how reliable P is, and/or what stage the cancer has reached. In this way, the human user can perform a diagnosis using the output of the method.

In another aspect, a method is provided for processing a set of images of a three-dimensional object, wherein each image in the set has an associated counterpart image. The method includes the steps of:
a) identifying one or more regions of interest in one or more of the images in the set of images;
b) for each region of interest identified in step a), identifying a reference region in the associated counterpart image;
c) cropping out the regions of interest and the reference regions identified in step b) from the counterpart images, thereby forming cropped pairs of images 1 . . . n;
d) feeding the cropped pairs of images from step c) to a deep learning model trained to make a prediction as to a state of the region of interest, and generating a prediction Pi, (i=1 . . . n) for each cropped pair; and
e) generating an overall prediction P from each of the predictions Pi;
wherein the deep learning model comprises a deep convolutional neural network which includes a feature extractor, a self-attention mechanism and a concatenation of information as to the global location of the region of interest to thereby inject global context information into the generation of the prediction Pi. The methodology is generally applicable to sets of images of 3D objects. In one possible example, the object is an anatomical structure.

The term "cropped out" is used to mean that the regions of interest are extracted from (i.e. isolated from) the rest of the images containing them.

The concepts above may alternatively be expressed as systems arranged to perform one of the methods, or as computer program products (e.g. recording media storing program instructions in non-transitory form, or downloadable software products) comprising instructions operative, when run by one or more computers, to cause the one or more computers to perform one of the methods.

In one further aspect, an artificial-intelligence method for performing diagnostic screening for patients disclosed. The method includes steps of: obtaining a set of one or more images from an initial screening test procedure; supplying the set of one or more images to an artificial-intelligence based classifier trained and validated to generate a score within a scoring regimen over a range which includes a Low threshold, and a High threshold, wherein the artificial-intelligence based classifier is configured to perform the method as explained above and in the following disclosure wherein the score is based on the overall prediction P, wherein the Low threshold is determined such that the negative predictive value is sufficient to consider all such patients having a score below the Low threshold as normal; wherein the High threshold is determined such that the specificity of a score is high enough such further diagnostic follow up and additional testing in accordance with a second diagnostic testing procedure is indicated as it would be if a trained expert human reader had deemed the patient's test result "positive"; generating a score for the set of one or more images with the artificial-intelligence based classifier; and reporting the score to a user, wherein if the score is above the High threshold the patient is referred to the second diagnostic testing procedure.

In still another aspect, a method of improving the workflow in a double reader diagnostic screening test is disclosed, which includes steps of: a) obtaining a set of one or more diagnostic images; b) receiving a result from a human expert reading the set of one or more diagnostic images; c) supplying the set of one or more diagnostic images to an artificial-intelligence based computerized system configured to perform the method for generating an overall prediction P as described herein, and generating a result based on the prediction of whether or not the set of one or more medical images are suspicious, e.g., likely positive for the presence of cancer; and d) wherein if the result generated by the human expert and the artificial-intelligence based computerized system are in agreement the result is treated as final (thereby avoiding the necessity of a second human reader in a double reading protocol), whereas in cases of disagreement, the set of one or more diagnostic images are furnished to a second human expert reader for interpretation.

conversely if the region of interest and corresponding reference region lowered the cancer probability prediction the boxes are rendered in green.

DETAILED DESCRIPTION

Typically, interpretation of imaging datasets is manually or semi-automatically performed by radiologists comparing the same region of the image across multiple time points or modalities. Automated approaches using deep learning can offer the ability to identify subtle cues across multiple images to assist a human user in the task of identifying and classifying cancer or other disease state.

When interpreting 2D or 3D medical images, radiologists will often view multiple large images or volumes in order to diagnose a patient's disease state, e.g. breast cancer from mammography/digital breast tomosynthesis, lung cancer from computed tomography or prostate cancer from magnetic resonance. Radiologists learn to fuse information across multiple images, and across disparate regions of the same image, in order to make a case-wide determination.

For example, when a region of one organ appears aberrant, they will frequently consult the corresponding region in the contralateral organ to determine whether it is part of the patient's normal pattern of tissue, exhibited on both organs, or an anomaly that may represent malignant growth. This often requires consulting a different image, as in the case of mammography, in which each breast is captured separately. (This process is analogous to the radiologists' consultation of the corresponding region in a previously acquired scan—a "prior" or longitudinal image—to identify change over time, which may indicate malignancy.)

Radiologists also make use of multiple views of the same tissue. This is analogous to having different camera angles on the same subject. Evidence can accumulate if a finding is noted on more than one image.

As the above two examples illustrate, radiologists home in on specific local findings but consult other regions, seeking the proper context in which to interpret these findings. In designing computer vision systems for interpreting medical images, this presents a challenge. Existing systems interpret images at a global scale, using the full image, or at a very local scale, using small subsets of the image. The former approach may encounter insufficient image resolution and have trouble providing pixel level attribution. On the other hand, local methods can be overly focused on small details and fail to adequately consider the broader or "global context" of the tissue, for example where a region of interest is positioned in the mammogram relative to the chest wall. The present disclosure addresses this deficiency.

Figure 1:
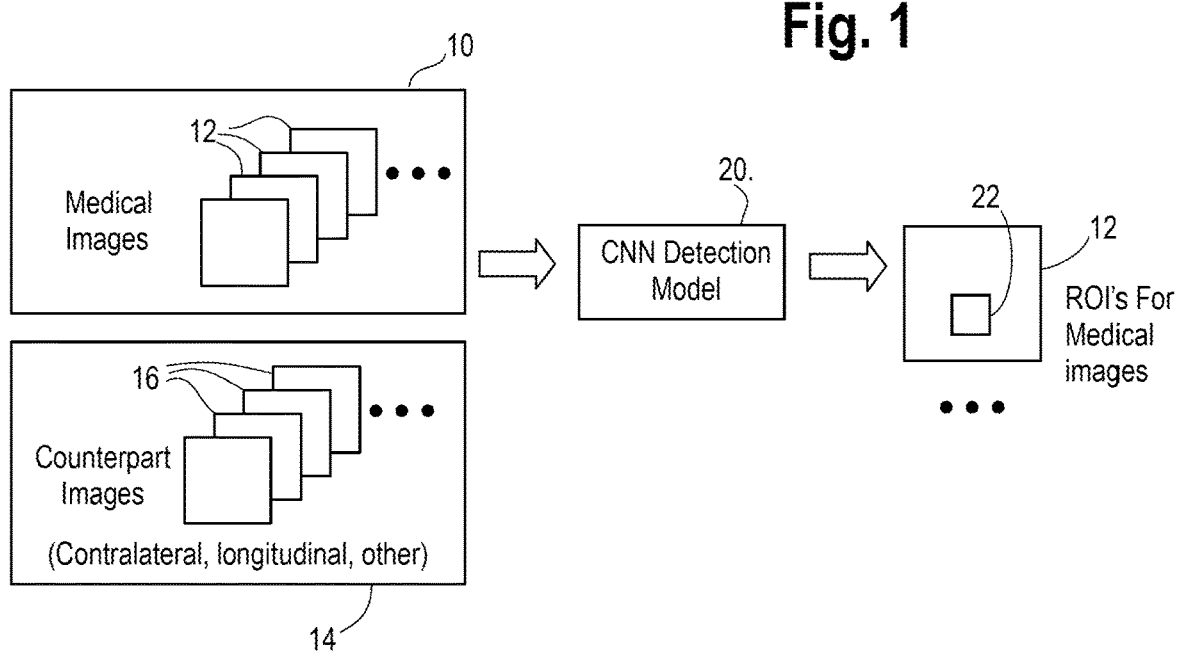
FIG. 1 is an illustration of a detection model identifying regions of interest in a set of images, which in one possible example is a set of medical images, e.g., mammograms.

With reference now to FIG. 1, we will describe our method of processing a set 10 of medical images 12. The set 10 of images 12 could for example take the form of a set of CT images of an anatomical structure, such as the chest, head, etc., or a set of mammograms, or a set of MRI images of a particular organ or joint, etc. The following example will be described for purposes of illustration and not limitation in the context of set 10 of digital mammogram images 12.

The set 12 is associated a set 14 of counterpart images 16. Each image 12 in the set 10 has an associated counterpart image 16, for example, a contralateral image, an image of the same anatomical area/structure/organ obtained by a different imaging modality, or a prior/longitudinal image of the same area/structure/organ. In a mammography example, the set 10 of images could be a set of four images obtained from the left breast in four different orientations (CC, MLO, ML, LM, conventional) and the associated counterpart images 16 are the contralateral images of the right breast obtained in the same four orientations.

The method includes a step of identifying one or more regions of interest (ROIs) (e.g., potentially cancerous lesions) in one or more of the images in the set of images 12. As shown in FIG. 1, the medical images 12 are supplied to a deep convolutional neural network 20 that has been trained from a multitude of images of the type in the set 10. This network functions as a detection model to detect ROIs in the images. As shown in FIG. 1, for a given image 12, a region of interest 22 is identified by a bounding box or border indicating that the tissue imaged in that region is potentially cancerous or has some other disease state for which the model is trained to identify. Each of the images 12 in the set 10 are processed by the model 20 in this way and if such ROIs are present they are identified and the pixel coordinates of the ROIs are stored. The design and architecture of the network 20 can take the form of the detection model described at length in the PCT application serial no. PCT/US2018/061956 filed Nov. 20, 2018, assigned to the assignee of this invention, the content of which is incorporated by reference herein. Other machine learning or neural networks trained to identify cancerous tissue in medical images are described in the scientific and patent literature and therefore a detailed description is omitted for the sake of brevity.

Figure 2:
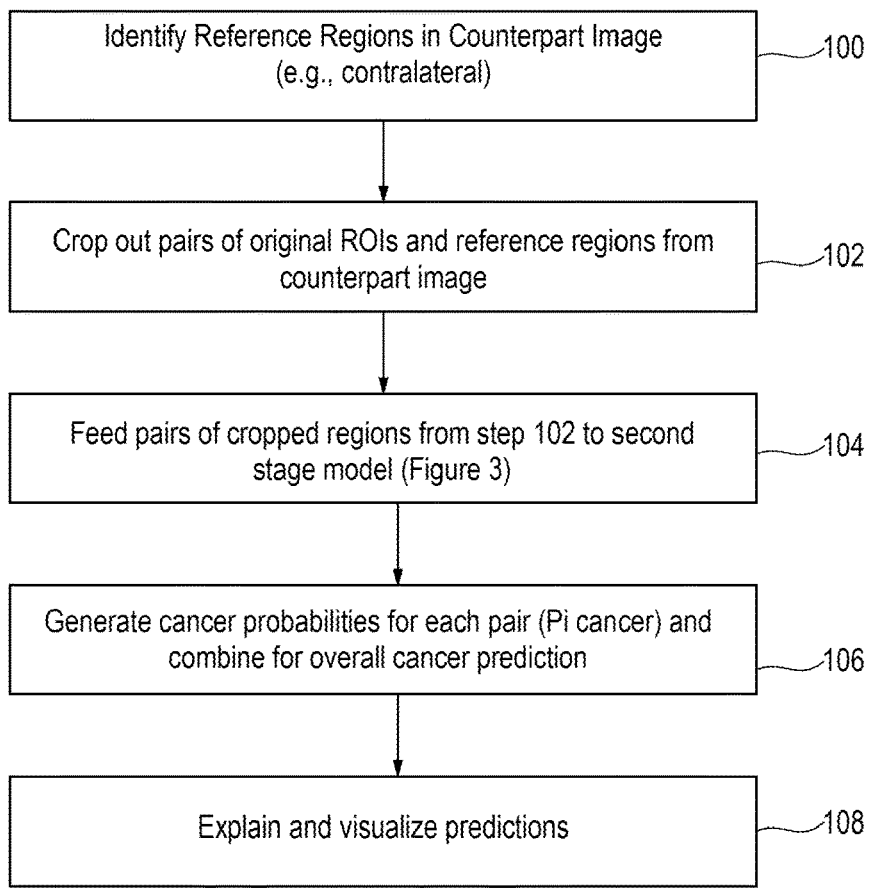
FIG. 2 is a flow chart showing a series of steps, performed using a computer, which processes a set of images and generates visualizations of predictions made by a deep learning model from the set of images.

The methodology then proceeds to the flow chart shown in FIG. 2. For each ROI found in the procedure of FIG. 1, in step 100 a reference region in the corresponding counterpart image (e.g., contralateral image) is identified. The process for identification of the reference regions in step 100 is shown in more detail in FIG. 4 and will be described later.

At step 102, we crop out the ROI/reference region pairs from the original image 12 in the set 10 and its associated counterpart image 16. Steps 100 and 102 are repeated for all of the ROIs that are found in the set 10 from the procedure of FIG. 1. Thus, the cropping out of the regions of interest and the reference regions forms cropped pairs of images 1 ... n. That is, for example if there are four images in the set 10, and four corresponding counterpart images 16, there could for example be 3 regions of interest identified in each of the four images 12 in the set 10; each region of interest in each image 12 has its associated reference region in the corresponding contralateral image 16, therefore n=12 (4×3) in this example.

Figure 3:
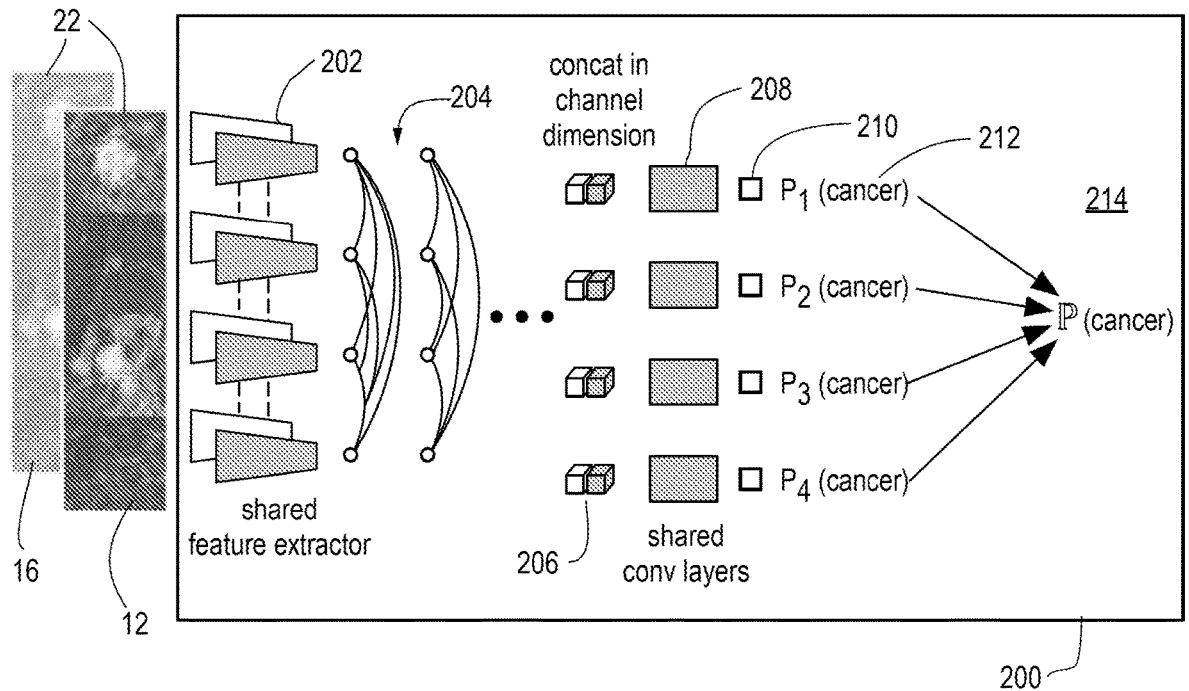
FIG. 3 is an illustration of a deep learning model used to generate predictions from the regions of interest identified by the model of FIG. 1.

Then, as indicated in step 104, we gather and feed all the n ROI/reference region pairs to a second stage model 200 shown in FIG. 3. The operation of this model will be described in detail below. Then, at step 106, the second stage model 200 generates probability predictions $P_i$ (e.g. in the range 0 to 1) for each ROI/reference region pair (i=1 ... N) and the probabilities are combined to generate an overall prediction P, e.g., using the noisy- or approach or some other procedure. At step 108, we generate visualizations of the predictions, typically in conjunction with a display of the image and counterpart image pairs, e.g., on a workstation used by a pathologist, see FIG. 6 and the discussion which follows.

Figure 4:
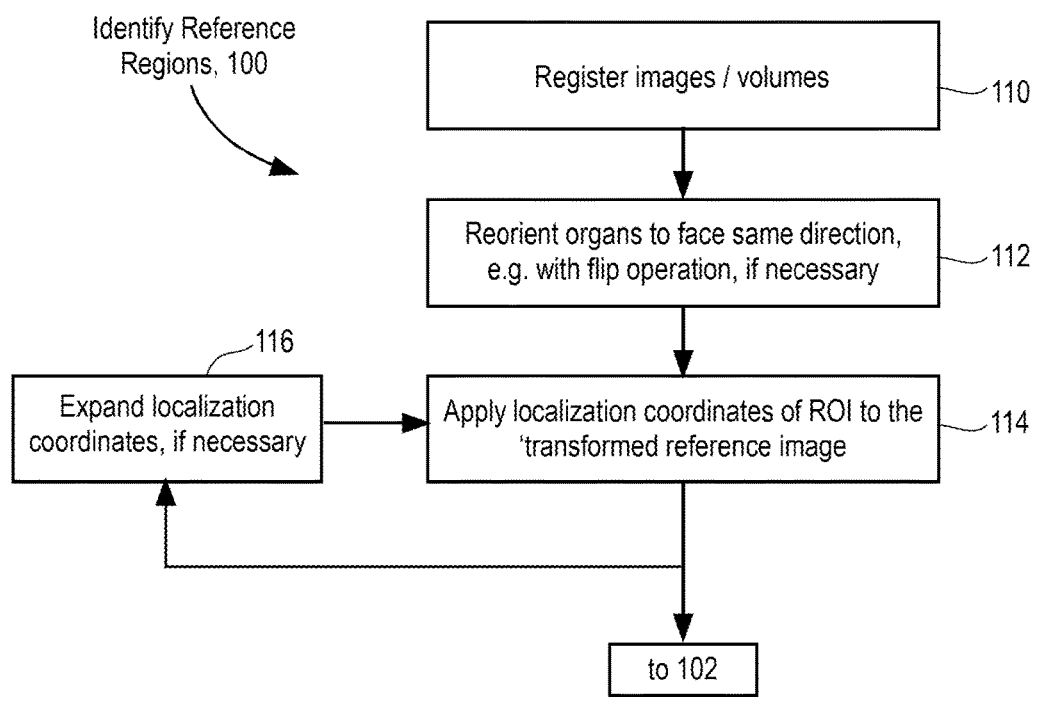
FIG. 4 is a flow chart showing a method of identifying reference regions in the counterpart images to the set of images of FIG. 1.
Figure 5:
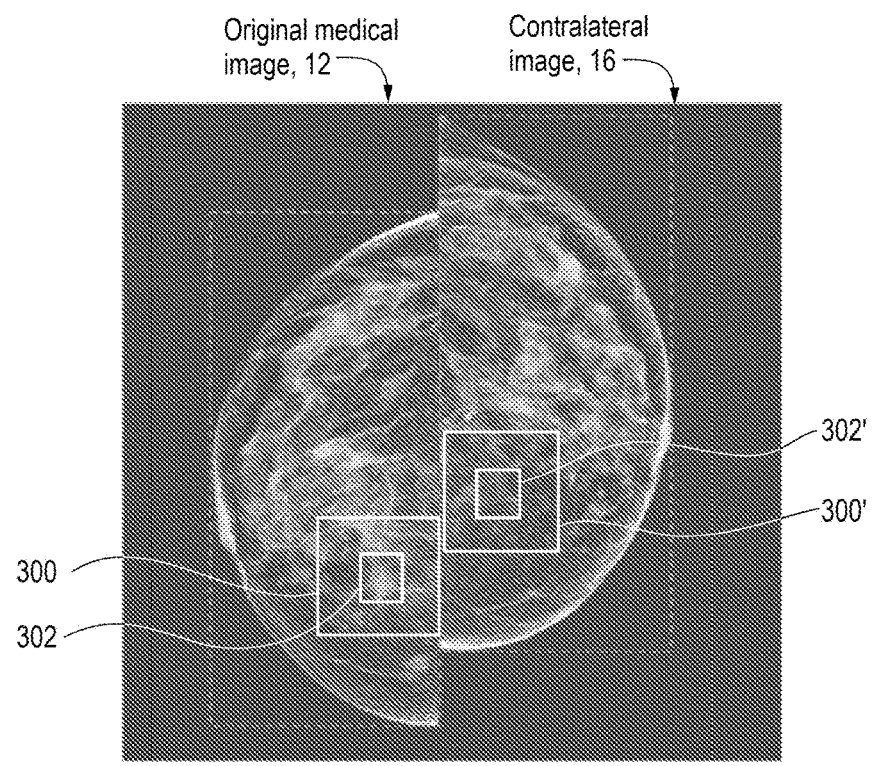
FIG. 5 is an illustration of a mammogram original image and its contralateral image showing two regions of interest in the original image and the corresponding reference regions in the contralateral image.

As noted above, in step 100 of FIG. 2, for any given input or original image 12 in the set 10 for which an ROI is detected in FIG. 1, we perform a step of identifying a "reference region" in the corresponding counterpart image 16. The term "reference region" is used to refer to a region in the counterpart image that corresponds spatially and/or anatomically to the area identified in the ROI. For example, with mammograms, if an ROI is found in a particular area, e.g., close to the chest wall in a particular position, of the right breast mammogram in a CC view, the reference region would be identified in the contralateral CC image in the same region in the left breast mammogram (i.e., also close to the chest wall), taking advantage of the symmetry found in contralateral mammograms. To identify this reference region as shown in FIG. 4, we first register the input and contralateral images/volumes (step 110). This can be achieved using one of the known rigid registration techniques or by aligning bounding boxes closely surrounding the organ of interest and cropping it out on multiple images/volumes, as depicted in FIG. 5 for mammograms. We then re-orient the contralateral image relative to the corresponding original image to face the same direction (i.e. such that corresponding anatomical structures in the two images appear to be the same, apart from natural random differences and differences due to pathological conditions), e.g., with a flip or rotation operation, if necessary (step 112). At step 114, we e then apply localization of the X/Y/Z coordinates of the ROI to the transformed reference image from step 112. If necessary to allow for potential errors in the registration method or acquisition protocol, expanded or wider localization coordinates are chosen around the original ROI and reference region previously selected, as indicated at step 116. Note that if the reference region can be identified in the original input image, some of these steps may not be necessary. For example, a standard chest X-ray shows both shoulders in a single image. In this case, the registration step 110 is not performed. However, a reorienting flip step may still be performed in step 112, e.g., to place the right shoulder joint in the same orientation as the left shoulder joint. FIG. 5 shows on the left hand side an original image 12 with bounding boxes 300 and 302 showing regions of interest, and in the right hand side the contralateral image (breast tissue) showing the corresponding reference regions 300' and 302' corresponding to ROIs 300 and 302.

As shown in FIG. 3, once all the cropped ROIs and corresponding reference regions have been obtained from the process of FIG. 2, step 102, the n pairs of ROI+reference region cropped images are supplied to the second stage model 200. This model is in the form of a deep learning model, for example deep convolutional neural network, which is trained to make a prediction of probability of disease state and generate a prediction Pi, (i=1 . . . n) for each cropped pair. The design and architecture of the model 200 can take the form of the second stage model described at length in the PCT application serial no. PCT/US 2018/061956 filed Nov. 20, 2018, assigned to the assignee of this invention. Machine learning models for making predictions about disease state from images are known in the art therefore a detailed description is omitted for the sake of brevity.

In essence, the model 200 includes a feature extractor 202 which is applied to every pair of regions (from the same or different modalities) separately. For example, if the feature extractor is implemented with a neural network of a type in which the input layer has a channel dimension greater than one, all images/volumes in a pair may be stored in separate channel dimensions of the input layer of the network or fused after the feature extractor.

Optionally, the model 200 includes a self-attention mechanism 204 (e.g. a Transformer architecture) which is applied to the unordered sequence of feature vectors (each corresponding to one region of interest) to allow multiple regions to influence each other's representations. For example, if two regions capture the same anatomy from different angles, this step lets them share information. For example, multi-head attention allows the model 200 to jointly attend to information from different representation subspaces at different positions. A description of self-attention mechanisms and Transformer architecture is contained in the publication of A. Vaswani et al., Attention Is All You Need, arXiv: 1706.03762v5 [csCL] 6 Dec. 2017, the content of which is incorporated by reference herein. The model includes feature vectors 206 which are concatenated in the channel dimension. Shared convolutional layers are depicted at 208. Once features are extracted from the pixel data, the global location of the region-of-interest (bounding box coordinates) can be concatenated as indicated at 210 (i.e. the features output by the feature extractor are concatenated with information indicating the global location of the region of interest) in order to inject more global context into the representation. For example, these features may encode the fact that this local patch was drawn from the "left posterior breast." The model 200 includes an output layer (not shown, conventional) that generates a probability (212 in FIG. 3) Pi for each of the i=1 . . . n ROI/reference region pair. These probabilities Pi are then combined into an overall probability P (214 in FIG. 3) of disease presence across all images using an aggregation mechanism such as the noisy-or function.

For example, the predictions Pi from each ROI+reference region pair is interpreted as the probability of malignancy for that ROI, and the final prediction (on the entire volume) is the probability that at least one of these ROIs is malignant:

$$P[\text{overall malignancy}] = 1 - \prod_{ROIs}(1 - P[ROI \text{ malignancy}]) \quad (1)$$

where P[ROI malignancy] is prediction Pi generated by the classification process for the given ROI+reference region pair. Thus, the equation for P is 1 minus the product of respective terms for each of the regions of interest, where each term is dependent upon the corresponding value of Pi.

While the above description has used as an example input or original images and counterpart images in the form of contralateral images, the methodology is essentially the same for other types of counterpart images, such as for example where the counterpart images are prior/longitudinal images, or images obtained of the same general area or organ using different imaging modalities, such as MRI, CT, PET scan etc.

As shown in step 108 of FIG. 2, the method includes an additional step of explaining and visualizing to the human user of the system to help them assess the image set 12, e.g., make a diagnosis. In particular, we contemplate generating a visualization of the set of medical images and the associated counterpart images including portions of the images corresponding to the cropped pair of images. Such visualization could be generated on a workstation or computing device used by a radiologist or other medical personnel. In general, if an ROI and its reference region pair is deemed to not increase the likelihood or a disease state prediction in the second stage model (i.e. the value of P given by the expression (1) above would not be higher if the term relating to that ROI were omitted from it, or the value of P is lower than a threshold), the localization coordinates of the patches corresponding to that group are transformed back onto the input images and visualized with a visual pattern or color associated with benign findings, e.g., green. Conversely, if an ROI and its reference region is deemed to increase the likelihood of a disease state prediction in the second stage model, the localization coordinates of the patches corresponding to that group are transformed back onto the input images and visualized with a visual pattern or color associated with potentially malignant findings, such as red. If the ROI and reference region pair had no effect on the prediction, then a third color, such as blue, could be used to display the ROI and reference region.

Figure 6:
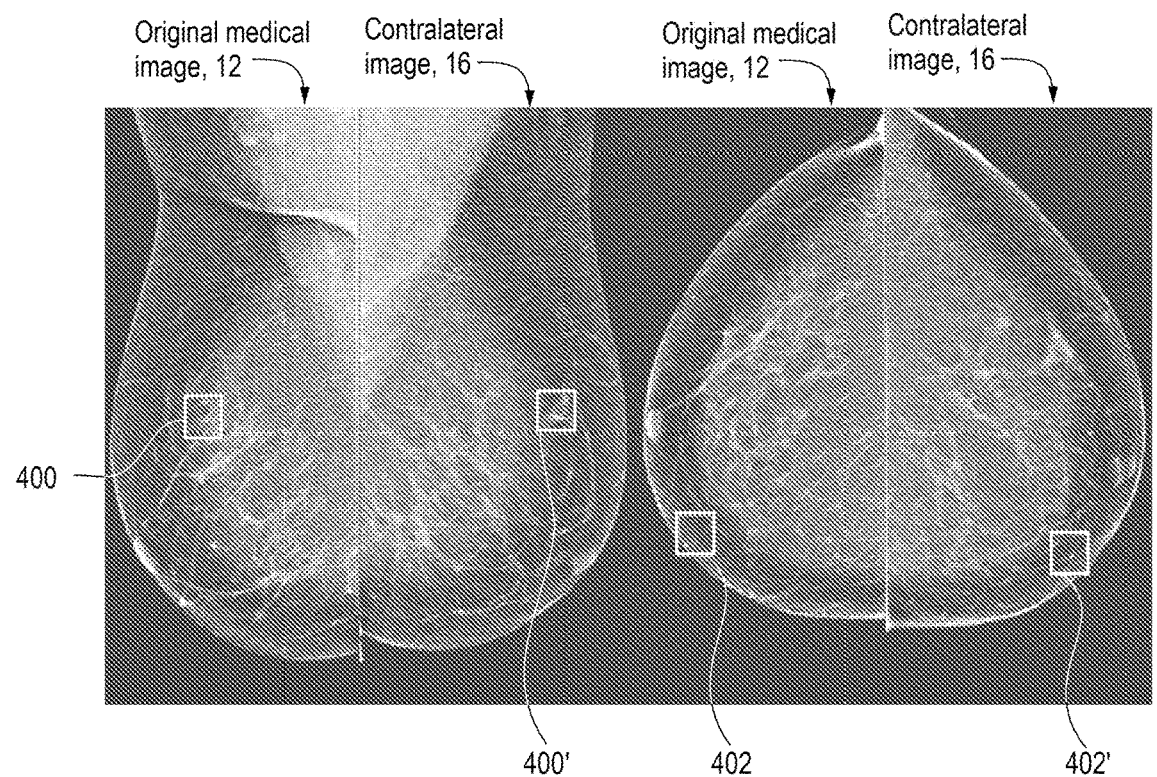
FIG. 6 is an illustration of two mammograms and associated contralateral images showing a region of interest and reference region bounded by a box. Color coding is added to the rendering or visualization of FIG. 6 on a computer monitor to indicate whether the region of interest contributed to raising or lowering the probability prediction generated by the model of FIG. 3. For example, if the region of interest and corresponding reference region increased the cancer probability prediction the boxes are rendered in red.

See for example FIG. 6. In this Figure, on the right, we see on the left hand side a mammogram image 12 and the contralateral mammogram image 16, and in the image 12 we generate a bounding box 402 which identifies the region of interest identified in the procedure of FIG. 1. The contralateral image 16 includes a bounding box 402' which identifies the corresponding reference region in the image 16. In this example, our method identifies a detection model's ROI proposal (FIG. 1) that ends up not influencing case's final disease state prediction generated by the second stage model (FIG. 3), and hence the boxes 402 and 402' are rendered in green. Conversely, on the left hand side of FIG. 6, we render the mammogram image 12 and the contralateral mammogram image 16, and in the image 12 we generate a bounding box 400 which identifies the region of interest identified in the procedure of FIG. 1 and bounding box 400' which identifies the reference region in the contralateral image 16. The ROI 400 causes the overall model prediction (from FIG. 3) to be positive (i.e., increase the probability of presence of cancer), after having been fed to the second stage model alongside corresponding reference region 400'. Therefore, the bounding boxes 400 and 400' are rendered in red. Plain text could be used to display this information, in addition or as an alternative to color rendering of the ROIs or borders thereof.

From the foregoing, it will be appreciated that in one aspect of this disclosure we have described a method of processing a set of mammograms, wherein each image in the set has an associated contralateral image. The method includes the steps of:
  a) identifying one or more regions of interest in one or more of the mammograms (FIG. 1);
  b) for each region of interest identified in step a), identifying a reference region in the associated contralateral image (FIG. 5; FIG. 2 step 100)
  c) cropping out the regions of interest and the reference regions identified in step b) from the contralateral images, thereby forming cropped pairs of images 1 . . . n (FIG. 2, step 102)
  d) feeding the cropped pairs of images from step c) to a deep learning model (FIG. 3) trained to make a prediction of probability of a cancerous disease state (FIG. 2 step 104) and generating a prediction Pi, (i=1 . . . n) for each cropped pair (FIG. 2 step 106) and
  e) generating an overall cancer prediction P from each of the predictions Pi (FIG. 3, FIG. 2 step 106); and
  f) generating a visualization of the mammograms and the associated contralateral images including portions of the images corresponding to the cropped pair of images (FIG. 6).

In the above method, the visualization generated in step f) further includes information indicating the manner in which a cropped pair of images contributed to the overall cancer prediction, such as described in conjunction with FIG. 6 or with addition of plain text in conjunction with the display of the images.

The above method is also applicable where, instead of a contralateral image, the counterpart images are prior or multimodal images.

While the above description has been provided in the context of medical images, it is possible to generalize the present disclosure as a method of processing a set of images of a three-dimensional object (not necessarily anatomical), wherein each image in the set has an associated counterpart image. The method includes the steps of:
  a) identifying one or more regions of interest in one or more of the images in the set of images (the region of interest need not be associated with a disease state);
  b) for each region of interest identified in step a), identifying a reference region in the associated counterpart image;
  c) cropping out the regions of interest and the reference regions identified in step b) from the counterpart images, thereby forming cropped pairs of images 1 . . . n;
  d) feeding the cropped pairs of images from step c) to a deep learning model trained to make a prediction as to a state of the region of interest, and generating a prediction Pi, (i=1 . . . n) for each cropped pair; and
  e) generating an overall prediction P from each of the predictions Pi.

The deep learning model in a preferred embodiment takes the form of a deep convolutional neural network which includes a feature extractor, a self-attention mechanism and a concatenation of information as to the global location of the region of interest to thereby inject global context information into the generation of the prediction Pi. The methodology is generally applicable to sets of images of 3D objects. In one possible example, the object is an anatomical structure.

Clinical Applications

We envision several different clinical applications of the methodology and system of this disclosure, including (1) using the deep learning models in a diagnostic screening and testing scenario, including integration of the AI into the workflow of diagnostic screening, and (2) improving the efficiency of double-reading workflow in population disease screening.

(1) System and Method for Semi-Automated Disease Screening with AI

Population screening has been an important tool in decreasing morbidity and mortality worldwide. Screening programs have been introduced for breast cancer, lung cancer, prostate cancer, diabetic retinopathy, pregnancy complications and many others. However, screening programs are very expensive, given large subpopulations who need to undergo an exam and whose results require interpretation. Long latency between screening and results delivery can adversely affect patient outcomes and cause significant patient anxiety.

Artificial intelligence (AI) systems for interpreting medical test results/imaging have been subject to intensive development in recent years, partly for the desire to decrease these costs and increase access to screening. While many teams presented human or superhuman performance in retrospective trials, few had an opportunity to be deployed, partly because of the difficulty in fitting an AI component into historically human-oriented workflows. For example, naïve inclusion of CAD systems in the workflow of mammographers has failed to deliver on its efficiency promise.

In accordance with our method, in the screening scenario, and as an example of system usage, we envision an initial, low-cost test is applied to check for any indication of disease. If the results indicate suspicion, a higher-cost procedure is applied. Although this second diagnostic procedure may carry more medical risks, it has better performance characteristics. For example, in the case of mammographic screening for breast cancer, patients with suspicious screening images are referred for more targeted imaging. In the case of worrying findings on low dose CT screening for lung cancer, patients may be escalated to a contrast-enhanced chest CT. Our method makes use of an AI-based classifier (essentially using the techniques of the model of FIG. 3 as described at length previously) which generates a score (or probability) based on images generated from an initial low cost screening test (e.g., routine mammography, including contralateral, multimodal or longitudinal images). The scores fall either below a low threshold (L), above a high threshold (H) or between the low and high thresholds.

The classifier is developed with retrospective validation results by an administrator/developer such that a classifier score threshold of High or H is determined over which the specificity is high enough such further diagnostic follow up and additional testing (typically using more expensive or invasive procedures) is worth the associated risk and cost, and as would be recommended by a human reader if the patient's test result was deemed "positive." For example, the administrator can choose an H threshold above which the positive predictive value is comparable with human expert readers. If a patient's score under the initial low cost screening test is above the H threshold, the patient is considered at risk and is referred for an immediate follow-up at a diagnostic workstation, e.g., for testing under a second or more costly or more invasive screening test. As stated above, the same would happen if the test result for the initial low cost screening test was deemed "positive" by a human reader, but using the AI and classifier feature of this disclosure there is much lower latency; there is no wait time waiting for a human reader to read the images from the initial diagnostic test.

If human interpretation is necessary to gate the application of the follow-up diagnostic test, a high suspicion signal from the classifier could be used to trigger urgent interpretation of the images. The low latency between the first and second tests means that many patients may need fewer visits to the clinic, reducing transit and scheduling costs.

Additionally, again given retrospective validation results, the administrator determines a classifier score threshold of Low or L, under which the negative predictive value is high enough to consider all such patients normal. For example, the administrator can choose an L threshold above which the sensitivity is comparable with human expert readers. If a patient's score under the initial low cost screening test is below the L threshold, the system implementing the classifier delivers a "negative" test result to the patient and their primary physician, and to the personnel or physician administering the initial low cost test, e.g., on a GUI.

Note that a human interpretation could eventually be rendered as usual, but the patient would receive immediate feedback from the automated classification, thus allaying the anxiety normally experienced waiting for high-latency test results. If the human interpretation is deemed more reliable, these results would ultimately supersede the preliminary classification, but the operating point L is selected so that such a reversal is unlikely.

If the score generated by the classifier is between the L and H scores, the case follows conventional workflow, with a human reader performing test result interpretation and deciding on the follow-up action, e.g., whether the second or more costly screening test is recommended.

Notes: the above description is for a binary classifier, but a similar procedure can be applied for a multiclass one, by binarizing the decision into (1) class of interest (e.g., positive) or (2) all other classes. Further, sometimes follow-up steps/testing requires additional information beyond a yes/no or positive/negative decision, such as localization or morphology of a finding in the case of medical imaging. In such a case, the AI screening model generates these outputs as well, for example using the localization methods which are known in the art for particular applications, such as lesion locations in retinal images, etc.

In an example of the screening scenario, an initial, low-cost test is conducted, such as routine mammography, to check for any indication of disease (here, breast cancer). If the results (i.e., score above H threshold) indicate suspicion, a higher-cost procedure is applied. Although this second diagnostic procedure may carry more medical risks, it has better performance characteristics. For example, in the case of mammographic screening for breast cancer, patients with suspicious screening images (i.e., score above the H threshold) are referred for more targeted imaging. In the case of worrying findings on low dose CT screening for lung cancer (score above the H threshold), the patients may be escalated to a contrast-enhanced chest CT.

As an example of a step-by-step implementation:

1. The test data (e.g. images) are acquired at a screening workstation. The patient's test/images are fed into an automation system (incorporating the models of FIGS. 1 and 3), which can be embedded in the imaging device, on a mobile device, on a PC, the cloud etc. The system runs the classifier and produces scores (e.g., in accordance with FIG. 3). If the classifier is multi-class, the scores are binarized.

2. If the score is below the threshold L, the system immediately delivers a negative test result to the patient and his/her primary physician. Such a decision is communicated to the personnel performing the test/imaging using a UI.

3. If the score is above the threshold H, the patient is considered at risk and is referred for an immediate follow-up at a diagnostic workstation. The same would happen if the test result was deemed positive by a human reader, but here there is much lower latency. Note that sometimes follow-up steps require additional information (other than just a yes/no decision, e.g. localization/morphology of a finding in case of medical imaging). In such case the AI screening model needs to produce these outputs as well.

4. If the score is between L and H, the case follows the usual workflow, with a human reader performing test results interpretation and deciding the follow-up action.

Note that the AI prediction can be used to gate a higher cost (or higher risk) screening procedure. Examples given include diagnostic mammograms or contrast-enhanced CT. Another such high cost "procedure" might be human interpretation itself. That is, if the score for the test data (images) is below L or above H, the test result of "negative" (score below L) or "positive" (score above H) is generated and in one possible implementation a human reader does not inspect the images at all. It is only in the case where the score is between L and H that a human reader is invoked to interpret the images.

One possible implementation or use case of this disclosure is "real time breast cancer screening." This means that some women can be offered same-day follow-up (diagnostic imaging and potentially biopsy) if their screening mammogram shows signs if suspicion. An alert will tell a radiologist on duy to follow up before the patient has left the screening center, collapsing what is currently a protracted process into a single visit. On the other side of the coin, for images that show a strong normal signal, the patient can be notified immediately that they are unlikely to have cancer, eliminating wait time and anxiety associated with it. This assessment will later be confirmed by a radiologist, but given the system's settings, it is unlikely to be overturned.

(2) Improving the Efficiency of Double-Reading in Population Disease Screening

In population screening for disease based on imaging tests (e.g., mammography or CT scans), most test results are interpreted by human experts. However, their performance is unreliable due to inherent subjectivity, inconsistent training, and lapses in attention or judgment. Accordingly, some screening programs (e.g. breast cancer screening programs throughout Europe) use a "double-reading" protocol. Here, two humans read each scan. (Sometimes this interpretation is sequential, such that the second reader has access to the first reader's opinion, but this need not be the case.) In cases of disagreement, a third reader is introduced to arbitrate the decision. While having additional oversight improves detection performance, it comes at a high cost: it more than doubles the amount of human effort required to process each scan. To offset the increased workload, such screening programs often reduce the frequency of screening, but this carries its own downsides.

Note that, in general, the screening outcome need not be binary, but a binary outcome is used for simplicity of illustration.

Our methodology proposes using an automated software system to alleviate some of the labor intensity of the double reading process. In particular, an automated, AI-based computerized system is proposed (based largely on the models described at length previously, see description of FIGS. 1 and 3 above) that receives a test result (e.g. a set of one or more medical images, e.g., mammograms) and renders a score reflective of a prediction of whether or not the medical images are suspicious, e.g., likely positive for the presence of cancer. This score is dichotomized to produce a binary decision: suspicious or not-suspicious (or the equivalent). The automated system is then applied after the first (human) reader renders his or her interpretation. When the automated system agrees with the first reader's decision, this decision is treated as final. In cases of disagreement, the typical double-reading process is invoked: a second (human) reader interprets the test and the chain of events proceeds as usual. (The computerized opinion may be made available to the subsequent readers.)

In this way, the computerized read is used to gate the double-reading process. If the computer-generated result confirms the first reader's opinion, a single human interpretation is trusted. This approach is intended to reduce the human resources required to implement double reading—the second (human) reading is avoided in cases of agreement between the first (human) reader and the result produced by the AI computer system.

If the AI computer system produces a confidence score for all of its predictions, this can be used as an additional "knob" on the gate. That is, we may only want to trust the first reader when the computer system confirms his or her decision with sufficiently high confidence. A higher confidence threshold means that more human effort will be required. This "knob" can be adjusted to attain the desired tradeoff in overall system performance and human resource requirements. The adjustment of the confidence score would typically be performed by an administrator of a system implementing the method.

We claim:

1. A method of processing a set of medical images, wherein each image in the set has an associated counterpart image, comprising the steps of:
   a) identifying one or more regions of interest in one or more of the images in the set of images;
   b) for each region of interest identified in step a), identifying a reference region in the associated counterpart image;
   c) cropping out the regions of interest and the reference regions identified in step b) from the counterpart images, thereby forming cropped pairs of images 1 . . . n;
   d) feeding the cropped pairs of images from step c) to a deep learning model trained to make a prediction of probability of disease state and generating a prediction $P_i$, (i=1 . . . n) for each cropped pair, wherein the deep learning model comprises a self-attention mechanism that allows the deep learning model to jointly attend to information from different representation subspaces at different positions, and wherein the deep learning model comprises a deep convolutional neural network which includes a concatenation of information as to a global location of the region of interest to thereby inject global context information into the generation of the prediction $P_i$;
   e) generating an overall disease prediction P from each of the predictions Pi; and
   f) generating a visualization of the set of medical images and the associated counterpart images including portions of the images corresponding to the cropped pair of images.

2. The method of claim 1, wherein the associated counterpart image comprises a contralateral image.

3. The method of claim 1, wherein the set of medical images comprises a set of mammogram images, and wherein the associated counterpart images comprise contralateral images.

4. The method of claim 1, wherein the associated counterpart image comprises a longitudinal image.

5. The method of claim 1, wherein the associated counterpart image comprises an image obtained by an imaging modality which is different from the modality used to generate the set of images.

6. The method of claim 1, wherein the visualization generated in step f) further includes information indicating the manner in which a cropped pair of images contributed to the overall disease prediction.

7. The method of claim 1, wherein the deep learning model further includes a feature extractor and the self-attention mechanism.

8. The method of claim 1, wherein the identifying of the one or more regions of interest in step a) is performed with a second deep learning model trained to identify the regions of interest.

9. The method of claim 1, wherein the associated counterpart image comprises a multimodal image.

10. A method of processing a set of images of a three-dimensional object, wherein each image in the set has an associated counterpart image, comprising the steps of:
   a) identifying one or more regions of interest in one or more of the images in the set of images;
   b) for each region of interest identified in step a), identifying a reference region in the associated counterpart image;
   c) cropping out the regions of interest and the reference regions identified in step b) from the counterpart images, thereby forming cropped pairs of images 1 . . . n;
   d) feeding the cropped pairs of images from step c) to a deep learning model trained to make a prediction as to a state of the region of interest, and generating a prediction Pi, (i=1 ... n) for each cropped pair; and e) generating an overall prediction P from each of the predictions Pi;

wherein the deep learning model comprises a deep convolutional neural network which includes a feature extractor, a self-attention mechanism and a concatenation of information as to a global location of the region of interest to thereby inject global context information into the generation of the prediction Pi.

11. The method of claim 10, wherein the associated counterpart image comprises an image of the three-dimensional object obtained by an imaging modality which is different from the modality used to generate the set of images.

12. The method of claim 11, wherein the set of images comprises a set of two-dimensional images of the three-dimensional object.

13. The method of claim 11, wherein the set of images comprises a set of three-dimensional images of the three-dimensional object.

* * * * *